(12) United States Patent
Chadwick et al.

(10) Patent No.: US 7,672,795 B1
(45) Date of Patent: *Mar. 2, 2010

(54) METHOD FOR SAMPLING SEEPAGE (75) Inventors: David B. Chadwick, San Diego, CA (US); Andrew Patterson, Lakeside, CA (US); Gregory J. Groves, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 173 days.

This patent is subject to a terminal disclaimer.

(21) Appl. No.: 11/970,066

(22) Filed: Jan. 7, 2008

Related U.S. Application Data (63) Continuation-in-part of application No. 11/266,523, filed on Nov. 3, 2005, now Pat. No. 7,424,375, which is a continuation of application No. 10/790,874, filed on Mar. 2, 2004, now Pat. No. 6,993,437.

(51) Int. Cl.
*G01F 1/00* (2006.01)
(52) U.S. Cl. ...................................................... 702/45
(58) Field of Classification Search .................. 702/45; 200/61.86; 137/625.17, 527, 884; 91/532; 251/367; 447/137; 73/863.01, 863.34; 356/237
See application file for complete search history.

(56) References Cited

U.S. PATENT DOCUMENTS

| 5,497,663 | A | 3/1996 | Reay et al. |
| 6,874,371 | B1 * | 4/2005 | Smith et al. ............... 73/861.23 |
| 6,993,437 | B1 * | 1/2006 | Chadwick et al. ............. 702/45 |
| 2005/0252306 | A1 | 11/2005 | Smith et al. |

* cited by examiner

*Primary Examiner*—Tung S Lau
*Assistant Examiner*—Xiuquin Sun
(74) *Attorney, Agent, or Firm*—Ryan J. Friedl; Kyle Eppele (57) ABSTRACT

A method includes the steps of providing a tidal seepage meter having a power supply, a controller capable of controlling the power supply according to a sampling schedule, a motor capable of receiving power from the power supply according to the sampling schedule, a selector valve having an input port and at least two outlet ports and capable of selecting an output valve according to the sampling schedule, a seepage chamber capable of receiving seepage and inputting seepage to the selector valve via the input port, and a first sample container and a second sample container capable of receiving seepage from the selector valve via the output valve, transferring the sampling schedule to the tidal seepage meter, positioning the tidal seepage meter in sediment; and sampling seepage according to the sampling schedule. The sampled seepage water may then be analyzed and the results may be displayed to a user.

19 Claims, 10 Drawing Sheets

METHOD FOR SAMPLING SEEPAGE

CROSS-REFERENCE TO RELATED APPLICATIONS

This application is a continuation-in-part of U.S. application Ser. No. 11/266,523, filed Nov. 3, 2005, entitled "Tidal Seepage Meter", now U.S. Pat. No. 7,424,375, which is a continuation of U.S. application Ser. No. 10/790,874, filed Mar. 2, 2004, entitled "Tidal Seepage Meter", now U.S. Pat. No. 6,993,437, the contents of both fully incorporated by reference herein.

FEDERALLY SPONSORED RESEARCH AND DEVELOPMENT

The Method for Sampling Seepage is assigned to the United States Government and is available for licensing for commercial purposes. Licensing and technical inquiries may be directed to the Office of Research and Technical Applications, Space and Naval Warfare Systems Center, San Diego, Code 2112, San Diego, Calif., 92152; voice (619) 553-2778; email T2@spawar.navy.mil. Reference Navy Case No. 98766.

BACKGROUND

The present inventive subject matter is generally related to the field of seepage meters. Seepage meters quantify variable rates of flow and chemical transport between groundwater and surface water. Typical seepage meters only obtain one sample per use, which increases cost and danger to divers when used to obtain multiple samples over a period of time. Therefore, a current need exists for a method to sample seepage using a seepage meter that can obtain multiple samples per use.

DETAILED DESCRIPTION OF SOME EMBODIMENTS

Figure 1:
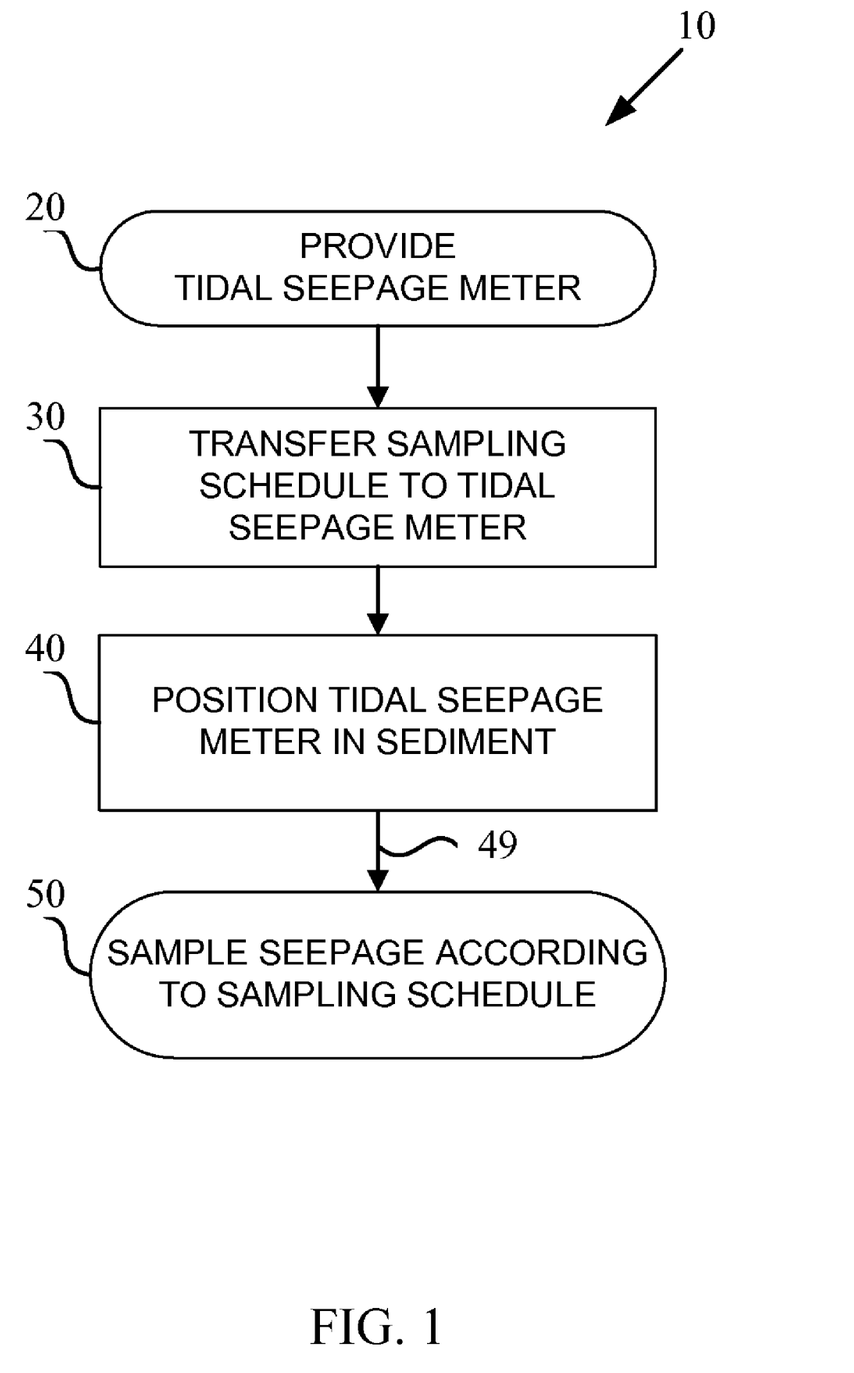
FIG. 1 shows a flow diagram of an embodiment of the method for sampling seepage.

FIG. 1 shows a flow diagram of an embodiment of the method for sampling seepage 10. Method 10 may begin at step 20, where a tidal seepage meter (TSM) is provided. Examples of TSMs that may be provided in accordance with step 20 are discussed with reference to FIGS. 6-10. By way of example, method 10 will be discussed with reference to TSM 500 as described in FIG. 9. In some embodiments, the steps of method 10 are performed using software stored in controller 530. In some embodiments, the steps of method 10 are performed using software stored in memory (not shown) within TSM 500.

Figure 10:
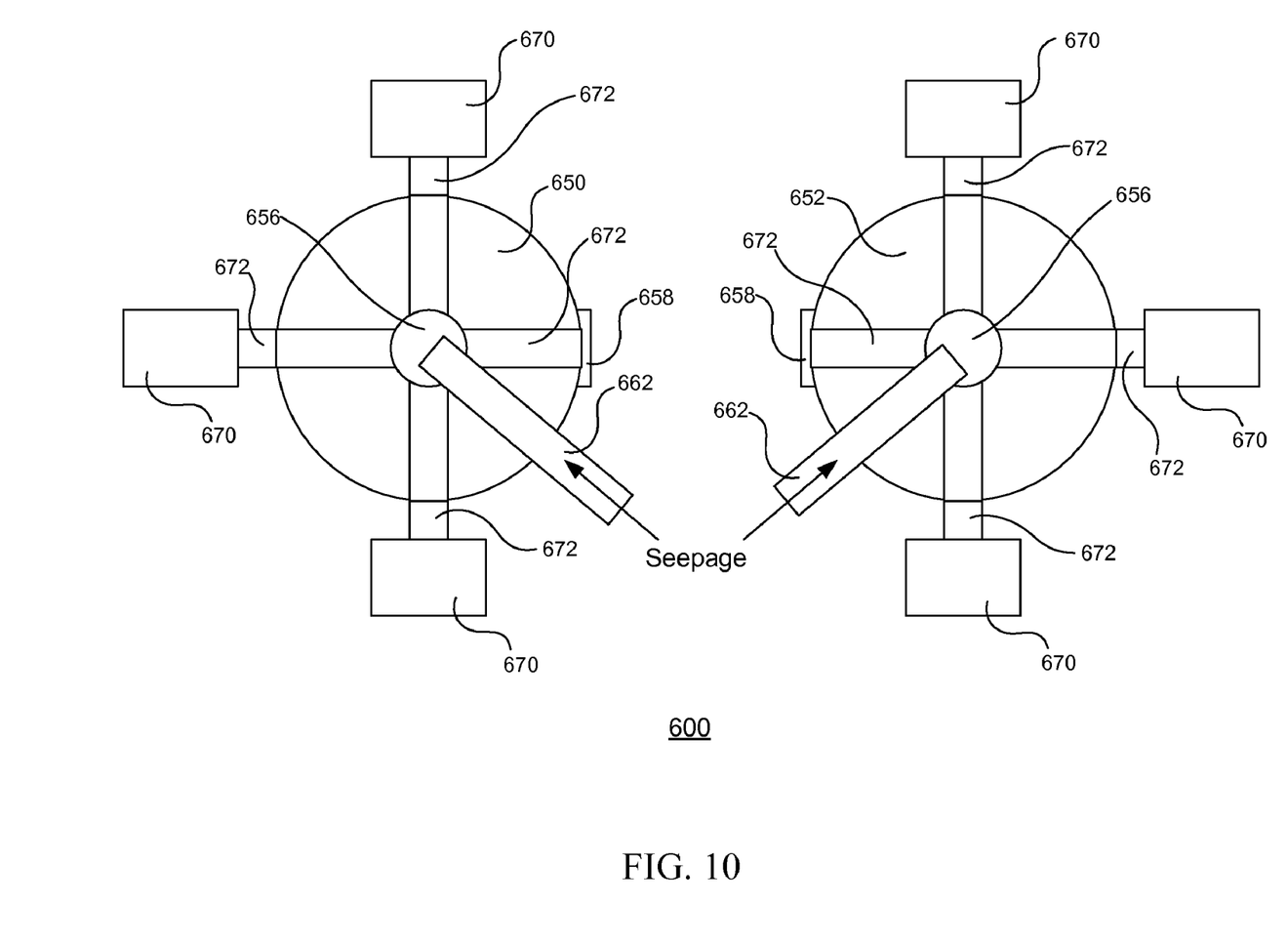
FIG. 10 shows a block diagram of an embodiment of a selector valve and sample container configuration for a tidal seepage meter that may be used to perform an embodiment of the method for sampling seepage.

Following step 20, method 10 may proceed to step 30, where a sampling schedule is transferred to TSM 500. The sampling schedule may have at least two sampling times. An example of a sampling schedule for a 24 hour tidal cycle is shown below in Table 1. The duration of the sampling schedules are not limited to 24 hours, but may vary as recognized by one having ordinary skill in the art. According to Table 1, at time zero, valves, such as 650 and 652 as shown in FIG. 10, may be at closed port position such that seepage may not substantially flow through outlet conduit 662 due to stopper 658. To collect the first sample, valves 650 and 652 may be rotated to a first position for a period of 0-4 hours. To collect the second sample, valves 650 and 652 may be rotated to a second position for a period of 4-8 hours. The sampling may continue until all six samples have been collected, after which, valves 650 and 652 may be rotated to closed port position such that stopper 658 prevents the flow of seepage through outlet conduit 662.

TABLE 1

| Tidal Cycle Sampling Schedule for 24 Hour Tidal Period | | |
|---|---|---|
| Sample Number | Time (Hrs.) | Condition |
| 0 | Off | Both valves at closed port |
| 1 | 0-4 | Valves at position 1 |
| 2 | 4-8 | Valves at position 2 |
| 3 | 8-12 | Valves at position 3 |
| 4 | 12-16 | Valves at position 4 |
| 5 | 16-20 | Valves at position 5 |
| 6 | 20-24 | Valves at position 6 |
| >6 | Off | Both valves at closed port |

Figure 6:
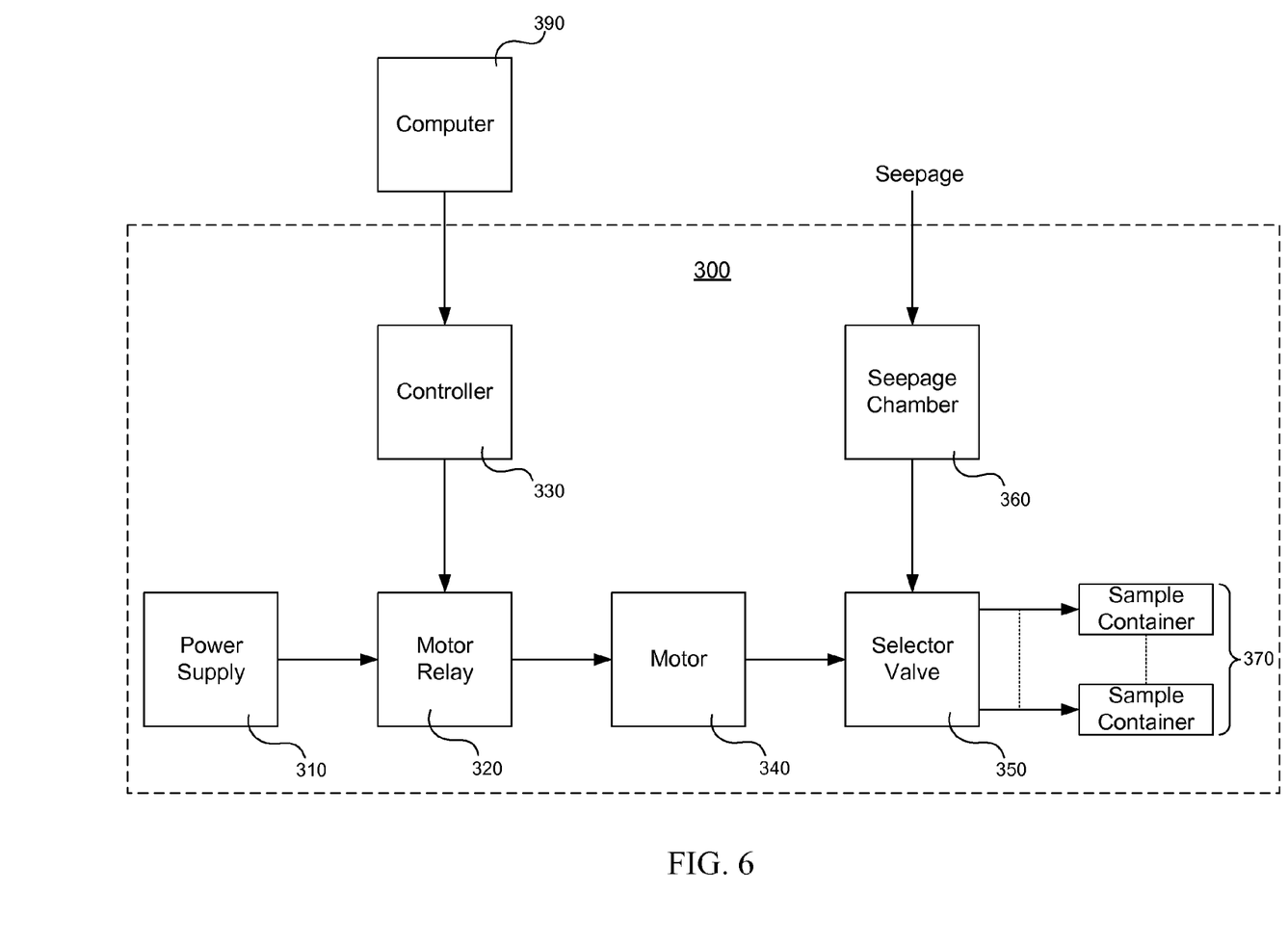
FIG. 6 shows a block diagram of an embodiment of a tidal seepage meter that may be used to perform an embodiment of the method for sampling seepage.

In one embodiment, method 10 may download a sampling schedule to controller 530 from a computer (see, for example, FIG. 6). In one implementation, the computer may be external to TSM 500. In another implementation, the computer may be internal to TSM 500. After step 30, step 40 may involve positioning TSM 500 in sediment. In one embodiment of method 10, TSM 500 is positioned in the sediment by embedding seepage chamber 560 substantially in the sediment so that the sediment surface is substantially flush with the top of the seepage chamber (see, for example, FIG. 8). In one embodiment of method 10, TSM 500 may be manually positioned within the sediment by a diver. In other embodiments, a machine may be used to position TSM 500 within sediment. TSM may be positioned in the sediment by being rotated into the sediment such that seepage chamber 560, on the sample port side, is approximately ¾" above the surface of the sediment, while the opposite side of seepage chamber 560 is flush with the sediment.

Figure 9:
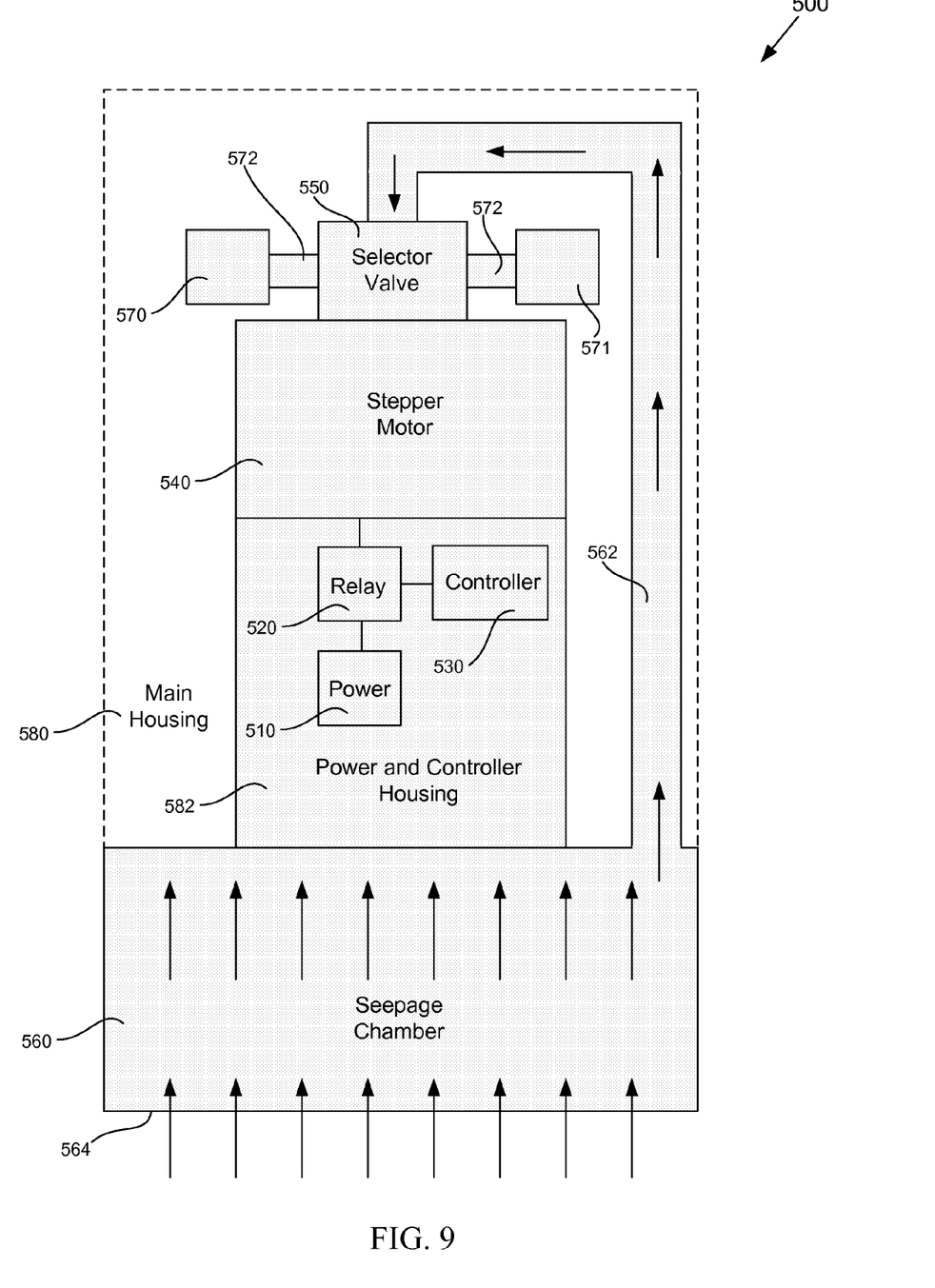
FIG. 9 shows a block diagram of an embodiment of a tidal seepage meter that may be used to perform an embodiment of the method for sampling seepage.

Following step 40, method 10 may proceed to step 50, where seepage is sampled according to the sampling schedule. In one embodiment, method 10 may send control signals to motor relay 520 to operatively couple power supply 510 and motor 540. Motor 540 may actuates selector valve 550. Motor 540 may be a stepper motor. Selector valve 550 may operatively couple seepage chamber 560 to a selected one of a plurality of sample containers 570 or 571. Actuation of selector valve 550 may then continue according to the sampling schedule.

Figure 2:
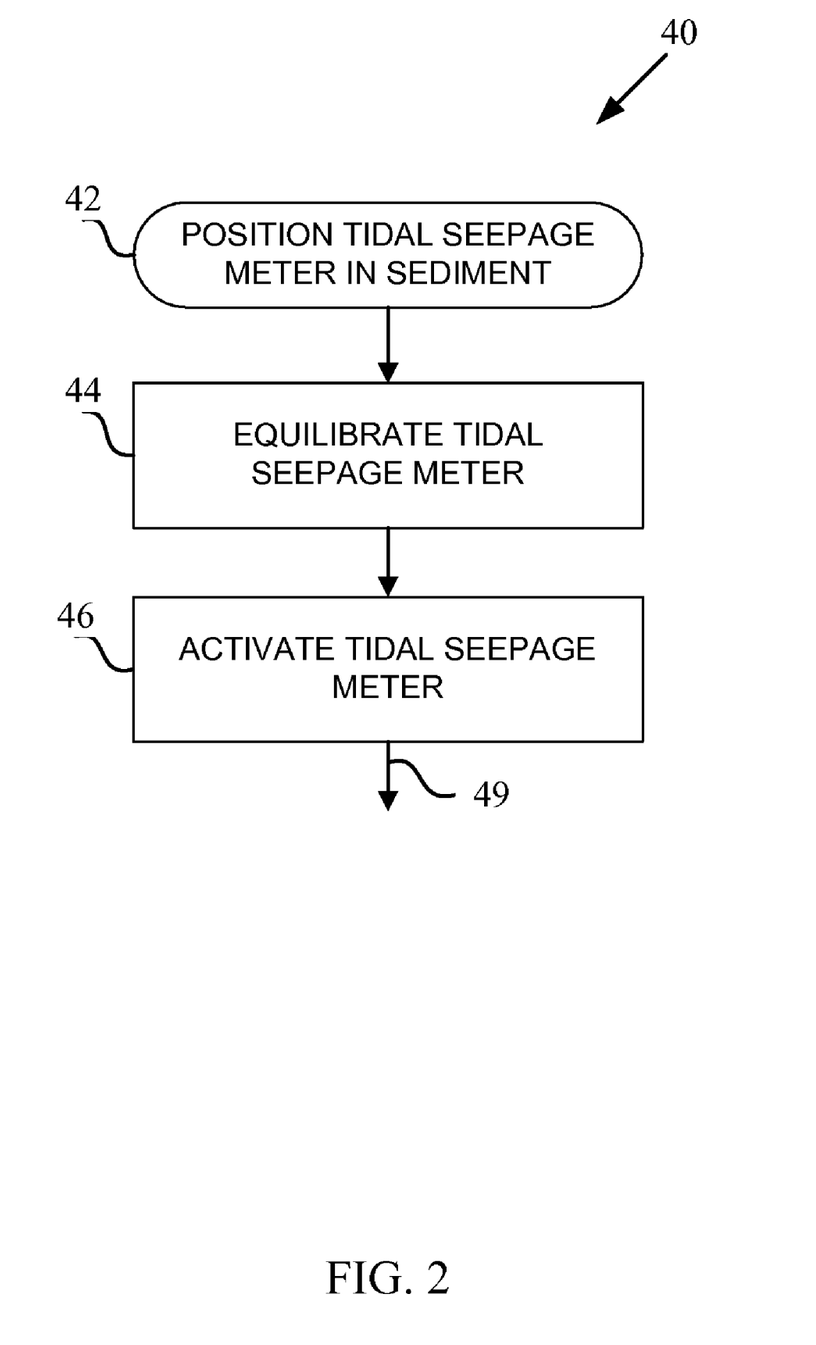
FIG. 2 shows a flow diagram of the step of positioning a tidal seepage meter in sediment, according to one embodiment of the method for sampling seepage.

FIG. 2 shows a flow diagram of an embodiment of step 40 of method 10. Step 40 may begin at step 42, where TSM 500 is positioned within sediment as discussed above. Following step 42, step 44 may involve equilibrating TSM 500. In one embodiment, step 44 equilibrates TSM 500 by waiting a predetermined amount of time to allow seepage flow conditions to return to normal. In one embodiment, TSM 500 may include an open port to allow seepage to pass through to the environment to help TSM 500 equilibrate. After step 44, step 40 may conclude at step 46, where TSM 500 is activated. In one embodiment of step 46, TSM 500 is activated by moving a magnet (not shown) mounted to the exterior of main housing 580 from an "off" position to an "on" position, which activates a magnetic switch (not shown) in main housing 580. Step 40 may then proceed to step 50 along flow path 49.

Figure 3:
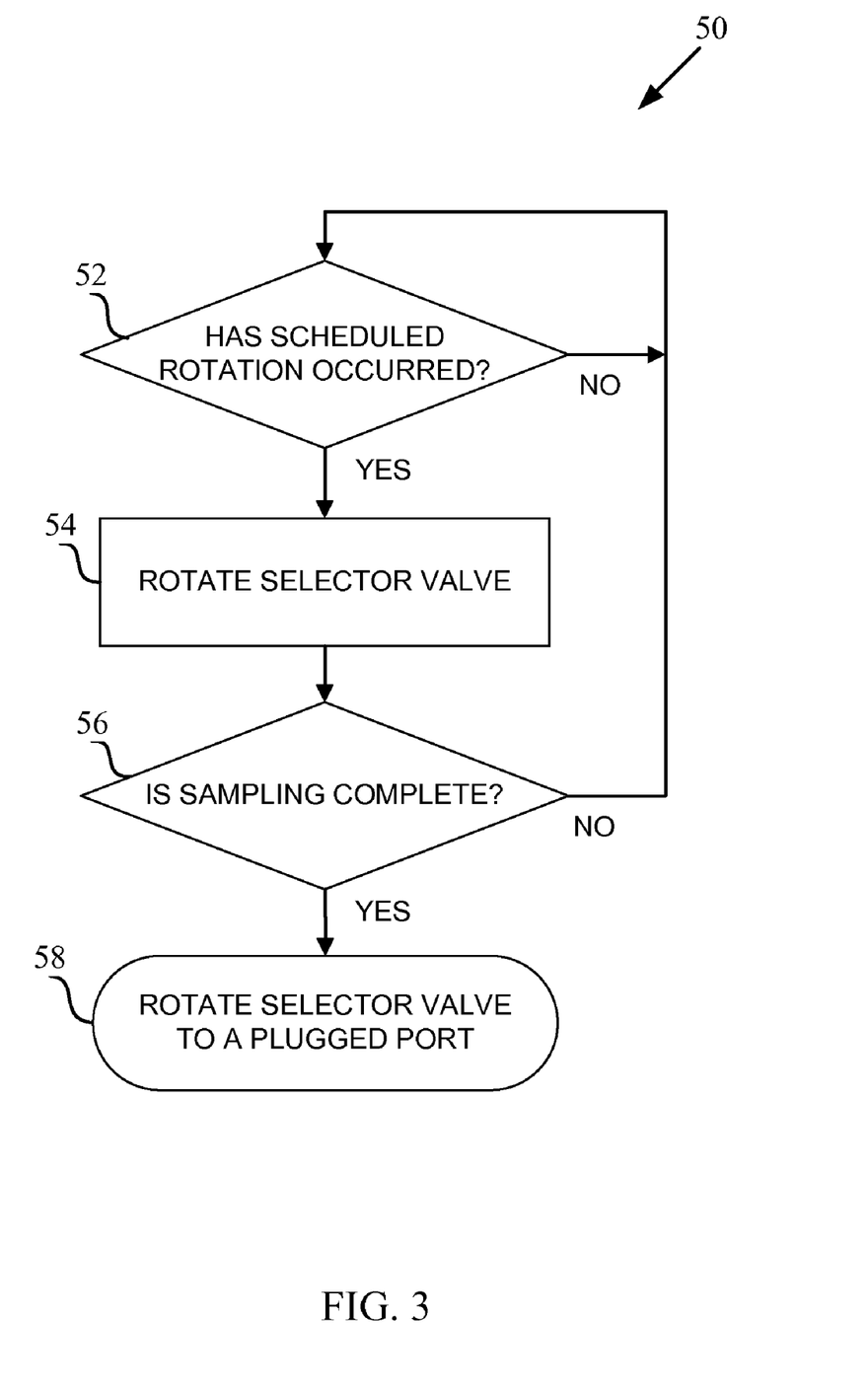
FIG. 3 shows a flow diagram of the step of sampling seepage according to the sampling schedule, according to one embodiment of the method for sampling seepage.

FIG. 3 shows a flow diagram of an embodiment of step 50 of method 10. Step 50 may begin at step 52, where a determination is made whether the scheduled rotation time has occurred. In one embodiment, the determination whether the scheduled rotation time has occurred may be performed by an internal clock or timer (not shown) onboard TSM 500. If the rotation time has not occurred, step 50 repeats step 52. If the rotation time has occurred, step 50 proceeds to step 54, where the selector valve is rotated. Following step 54, step 56 involves determining whether sampling is complete. In one embodiment, the determination whether sampling is complete may be performed by the internal clock or timer onboard TSM 500, by determining whether the scheduled sampling period has ended. If it is determined that sampling is not complete, step 50 returns to step 52. If sampling is complete, step 50 may proceed to step 58. Step 58 may involve rotating selector valve 550 to a plugged port, such as stopper 658 (see FIG. 10).

Figure 4:
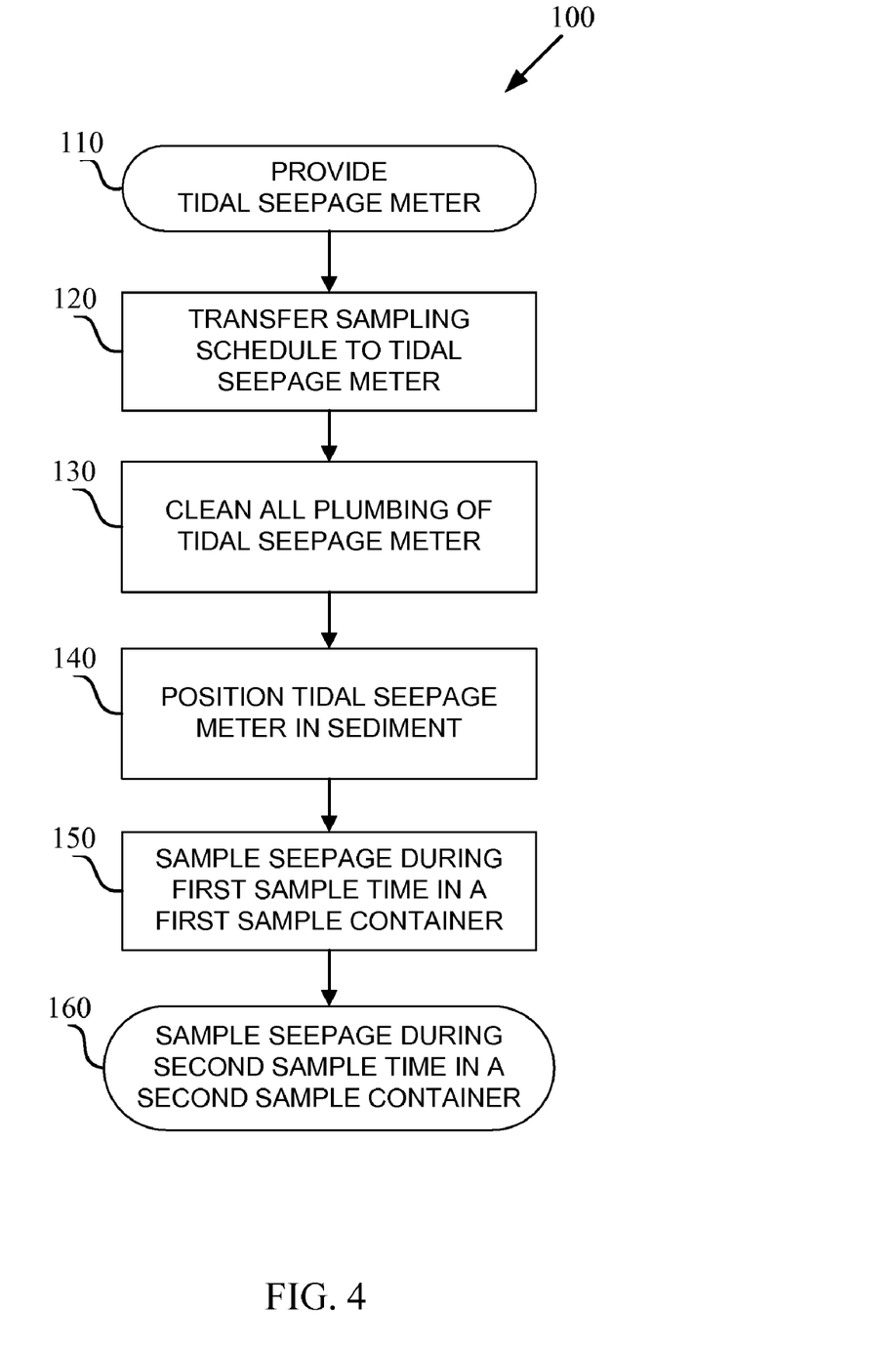
FIG. 4 shows a flow diagram of another embodiment of the method for sampling seepage.

FIG. 4 shows a flow diagram of an embodiment of the method for sampling seepage 100. Method 100 may begin at step 110, where a tidal seepage meter (TSM) is provided. Examples of TSMs that may be provided in accordance with step 110 are discussed with reference to FIGS. 6-10. By way of example, method 100 will be discussed with reference to TSM 500 as described in FIG. 9. In some embodiments, the steps of method 100 are performed using software stored in controller 530. In some embodiments, the steps of method 100 are performed using software stored in memory (not shown) within TSM 500.

Following step 110, method 100 may proceed to step 120, where a sampling schedule is transferred to TSM 500. In one embodiment, step 120 may involve downloading a sampling schedule to controller 530 from a computer. The sampling schedule may have at least two different sampling times. After step 120, step 130 may involve cleaning all of the plumbing of TSM 500. Step 130 may involve filling all of the plumbing of TSM 500 with fresh water, programming controller 530 to activate motor 540 every few minutes, connecting a reservoir of cleaning solution, such as diluted detergent, to the inlet line of TSM 500, activating TSM 500 to sequence the valves while the cleaning solution flows through the plumbing, and repeating the process with a pure freshwater rinse. Next, step 140 may involve positioning TSM 500 in sediment. Step 140 may be performed similar to step 40 of method 10. Following step 140, method 100 may proceed to step 150, where seepage is sampled during a first sampling time in a first sample container 570. For example, seepage may be collected for a 2 hour time period in the first container 570. Method 100 may then proceed to step 160, where seepage is sampled during a second sampling time in a second sample container 571. For example, seepage may be collected for another 2 hour time period in the second container 571.

Figure 5:
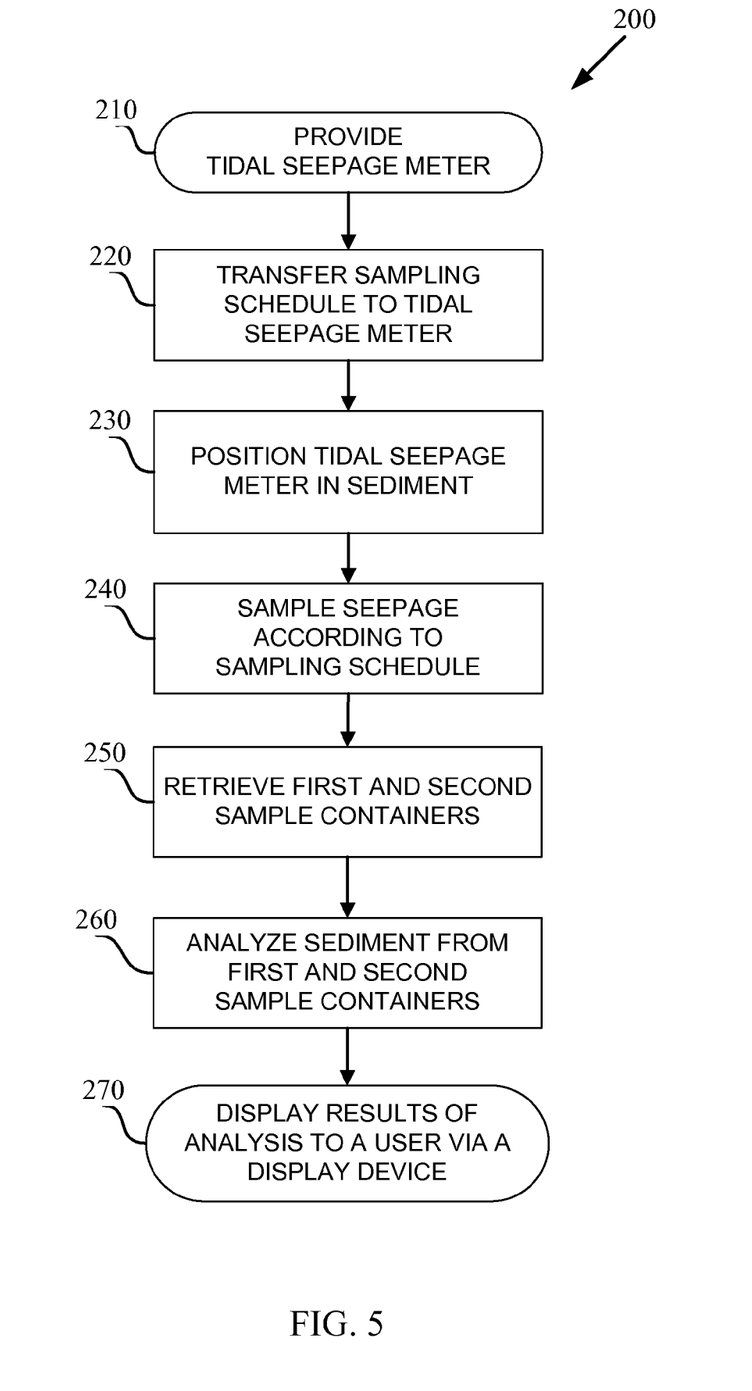
FIG. 5 shows a flow diagram of another embodiment of the method for sampling seepage.

FIG. 5 shows a flow diagram of an embodiment of the method for sampling seepage 200. Method 200 may begin at step 210, where a tidal seepage meter (TSM) is provided. Examples of TSMs that may be provided in accordance with step 210 is discussed with reference to FIGS. 6-10. By way of example, method 200 will be discussed with reference to TSM 500 as described in FIG. 9. In some embodiments, the steps of method 200 are performed using software stored in controller 530. In some embodiments, the steps of method 200 are performed using software stored in memory (not shown) within TSM 500.

Following step 210, method 200 may proceed to step 220, where a sampling schedule is transferred to TSM 500. In one embodiment, step 220 may involve downloading a sampling schedule to controller 530 from a computer. The sampling schedule may have at least two sampling times. After step 220, step 230 may involve positioning the tidal seepage meter in sediment. Step 230 may be performed similar to step 40 of method 10. Following step 230, method 10 may proceed to step 240, where seepage is sampled according to the sampling schedule. Step 240 may be performed similar to step 50 of method 10. After step 240, step 250 may involve retrieving a first sample container 570 and a second sample container 571. In one embodiment, 250 may involve removing first and second sample containers 570 and 571 from TSM 500, after TSM 500 has been retrieved. Next, step 260 may involve analyzing the seepage water from first sample container 570 and second sample container 571 to determine properties of the sampled seepage water. The seepage water from first and second sample containers 570 and 571 may be analyzed using standard Environmental Protection Agency chemical analysis methods for a variety of applications. For example, the sampled seepage water may be tested to determine the presence or absence of volatile organic contaminants, metals, and/or hydrocarbons. The analysis may be performed by a computer or other analysis device as recognized by one having ordinary skill in the art. Following step 260, step 270 may involve displaying the properties of the sampled seepage to a user via a display device. As an example, the display device may be a computer display or other display device recognized by one having ordinary skill in the art.

FIG. 6 shows a block diagram of an embodiment of a tidal seepage meter (TSM) 300 that may be used with a method for sampling seepage, such as methods 10, 100, and/or 200 as discussed herein. TSM 300 may include a power supply 310, motor relay 320, controller 330, motor 340, selector valve 350, seepage chamber 360 and at least two sample containers 370. Controller 330 may be operatively coupled to motor relay 320. Controller 330 may input control signals to components such as motor relay 320. In one embodiment, controller 330 may include a circuit board with interpreter chip, EEPROM, 5-volt regulator, reset circuit, and resonator. In one embodiment, controller 130 may be a BASIC STAMP II® by PARALLAX INC.

Controller 330 may control the sampling of TSM 300 according to a sampling schedule. A sampling schedule is a time schedule that designates desired times for obtaining samples. In one embodiment, a sampling schedule may obtain six total samples taken at four-hour intervals, which represents a one-day tidal cycle. In one embodiment, controller 330 may obtain sampling schedules from computer 390. In one embodiment, computer 390 may download sampling schedules to controller 330 via an interface link such as six-wire cable, optical, infrared and radio frequency links. In one embodiment, computer 390 may be contained within TSM 300. In one embodiment, TSM 300 may temporarily link to computer 390 to receive sampling schedules. In one embodiment, controller 330 may include an activation signal to enable/disable a power supply (e.g., power supply 310 and battery relay control signals). Power supply 310 may be operatively coupled to motor relay 320. Power supply 310 may be AC or DC power supplies. Examples of power supplies 310 may include DC batteries and AC generators. In one embodiment, power supply 310 may be a 12VDC gel cell battery rated at 1.2 amp hour. Power supply 310 may input voltage signals to motor relay 320.

Motor relay 320 may be operatively coupled to power supply 310, controller 330 and motor 340. Motor relay 320 may be capable of receiving control signals from controller 330. In one embodiment, motor relay 320 is a solid state AC relay with a control line rated at 3-32 VDC, 3.4 microamps at 5 VDC. Motor relay 320 may operatively couple power supply 110 and motor 140 when activated by control signals from controller 330, which is according to a sampling schedule. Motor 340 may operatively coupled to motor relay 320 and selector valve 350. Motor 340 may receive voltage signals from power supply 310 via motor relay 320 according to a sampling schedule. Examples of motors 340 may include stepper motors, hydraulics, and spring-driven mechanisms. In one embodiment, motor 340 may be an AC motor. In one embodiment, motor 340 may be a DC motor. In one embodiment, motor 340 may be a 90-degree stepper motor operating at 115 VAC. In one embodiment, motor 340 may be a 90-degree stepper motor operating at 12 VDC. In one embodiment, motor 340 may be unidirectional, NEMA 4 enclosure rated at 69VA total power, 80 lb.-in. torque and 2 sec./90-degree rotation. Motor 340 may actuate selector valve 350 when operatively coupled to power supply 310 via motor relay 320.

Seepage chamber 360 may be operatively coupled to selector valve 350. Seepage chamber 360 may receive seepage (i.e., water that is pushed through the interstitial spaces of marine or aquatic sediments by a hydraulic gradient formed between groundwater and offshore water levels) from sediment. Seepage chamber 360 may receive seepage through an open end and outputs seepage through an outlet. In one embodiment, seepage chamber 360 may be a semi-enclosed chamber (e.g., a drum cut in half having a closed end and an open end with an outlet drilled in the closed end, which is opposite of the open end). In one embodiment, seepage chamber 360 may be a funnel. In one embodiment, seepage chamber 360 may be a 9-inch bottom section of an 18-inch diameter SDPE container with a 2-inch threaded plug as an outlet. In one embodiment, seepage chamber 360 may further comprise an outlet conduit operatively coupled to the outlet. The outlet conduit may direct seepage to components such as selector valve 350. In one embodiment, the outlet conduit may comprise ½-inch TEFLON® compression fitting. Seepage chamber 360 may input seepage to selector valve 350.

Selector valve 350 may be operatively coupled to motor 340, seepage chamber 360 and sample containers 370. Selector valve 350 may receive seepage from seepage chamber 360. Selector valve 350 may actuate via motor 340 according to a sampling schedule. Selector valve 350 may include an inlet port and at least two outlet ports. Selector valve 350 may operatively couple the inlet port to one of the at least two outlet ports according to a sampling schedule. In one embodiment, selector valve 350 may comprise a six-way selector valve having one inlet port and six outlet ports. In one embodiment, selector valve 350 may comprise a four-way selector valve having one inlet port and four outlet ports. In one embodiment, selector valve 350 may comprise two four-way selector valves. In one embodiment, selector valve 350 may be a ½-inch four-way selector valve comprising 316 stainless steel bar stock with TEFLON® sleeve around rotor. In one embodiment, the inlet port of selector valve 350 may be operatively coupled to the outlet of the seepage chamber 360. In one embodiment, the inlet port of selector valve 350 may be operatively coupled to the outlet of the seepage chamber 360 via an outlet conduit. In one embodiment, motor 340 may rotate selector valve 350 90 degrees per sample time. Selector valve 350 may input seepage to one of the plurality of sample containers 370.

Sample containers 370 may be operatively coupled to selector valve 350. Sample containers 370 may be vessels for containing seepage samples. Those skilled in the art shall recognize that TSM 300 may comprise multiple sample containers 370 without departing from the scope or spirit from the present invention. In one embodiment, sample containers 370 comprise TEFLON® gas sampling bags. Sample containers 370 may receive seepage from seepage chamber 360 via selector valve 350. In one embodiment, a separate sample container 370 may be operatively coupled to each outlet port of selector valve 350. In one embodiment, separate sample containers 370 may be operatively coupled to selected outlet ports of selector valve 350.

As an example of how to operate TSM 300, computer 390 may download a sampling schedule to controller 330 of TSM 300. TSM 300 may then be positioned in sediment. Seepage may enter seepage chamber 360. Controller 330 may activate motor relay 320 according to the sampling schedule. Motor relay 320 may then provide electrical coupling between power supply 310 and motor 340 when activated (e.g., activated for 2 seconds at 1400 HRS). When electrically coupled to power supply 310, motor 340 may actuate selector valve 350, which may select an outlet port or, in one embodiment, a next outlet port. Seepage chamber 360 may input seepage to an inlet port of selector valve 350. Selector valve 350 may then input seepage to one of a plurality of sample containers 370 via a selected outlet port. Controller 330 may re-activate motor relay 320 according to the sampling schedule to provide a desired number of samples.

Figure 7:
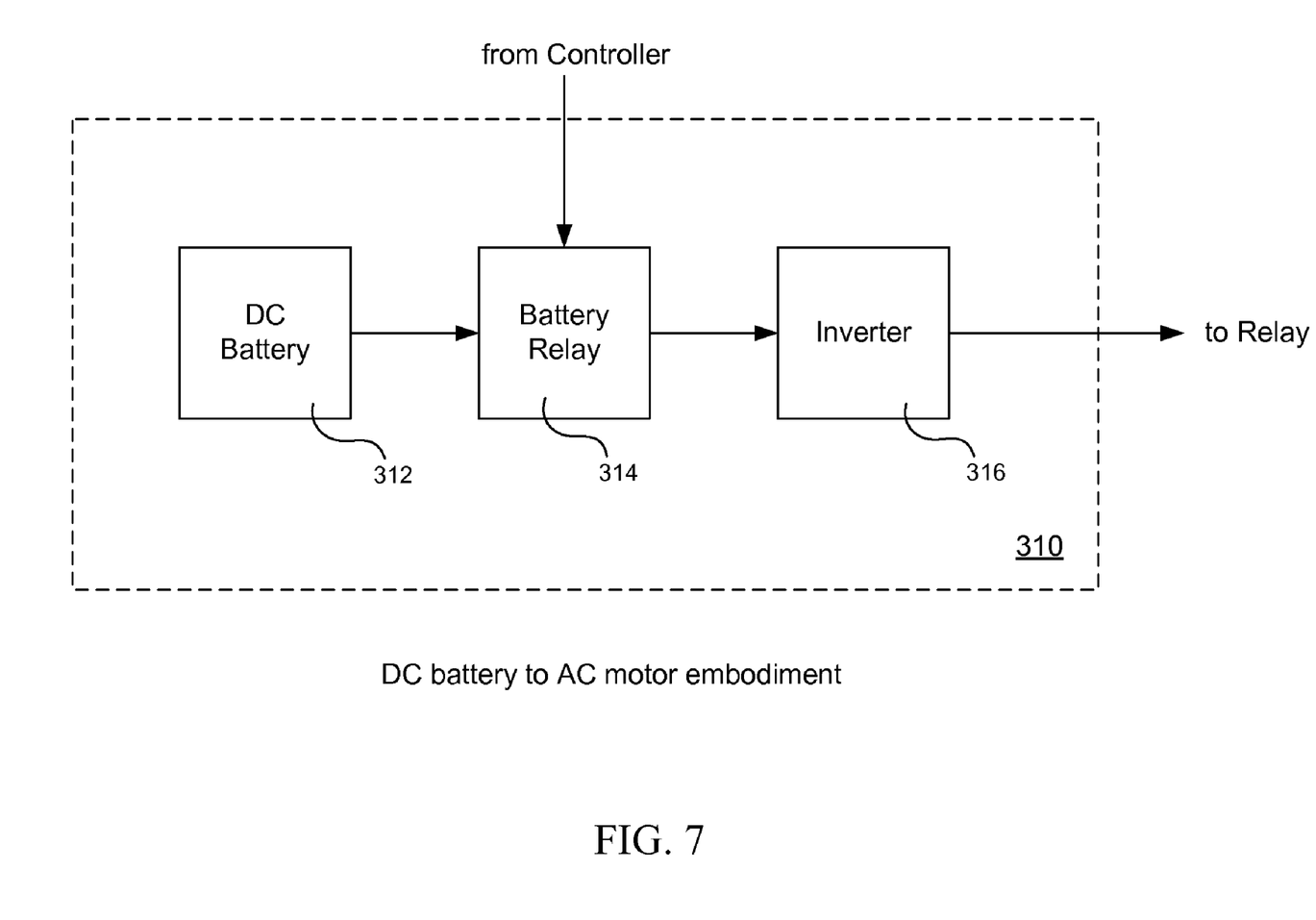
FIG. 7 shows a block diagram of an embodiment of a power supply that may be used in a tidal seepage meter that may be used to perform an embodiment of the method for sampling seepage.

FIG. 7 shows a block diagram of an embodiment of a power supply 310 that may be used with a method for sampling seepage, such as methods 10, 100, and/or 200 as discussed herein. Power supply 310 may include DC battery 312, battery relay 314 and inverter 316. In one embodiment, DC battery 312 may be a 12V DC gel battery rated at 1.2 amp hour. DC battery 312 may be operatively coupled to battery relay 314. Battery relay 314 may be capable of receiving control signals from a controller. In one embodiment, battery relay 314 is a solid state DC relay with a control line rated at 3.5-32V DC, 1.6 microamps at 5V DC. Battery relay 314 may be operatively coupled to inverter 316. Inverter 316 may be capable of inverting a DC signal to produce an AC signal. In one embodiment, inverter 316 converts 12V DC to 115V AC at 60 Hz. In one embodiment, inverter 316 provides 115V AC at 140 W. In one embodiment, inverter 316 is rated for 400 W surges. Inverter 316 may input an AC signal to motor relay 320.

Figure 8:
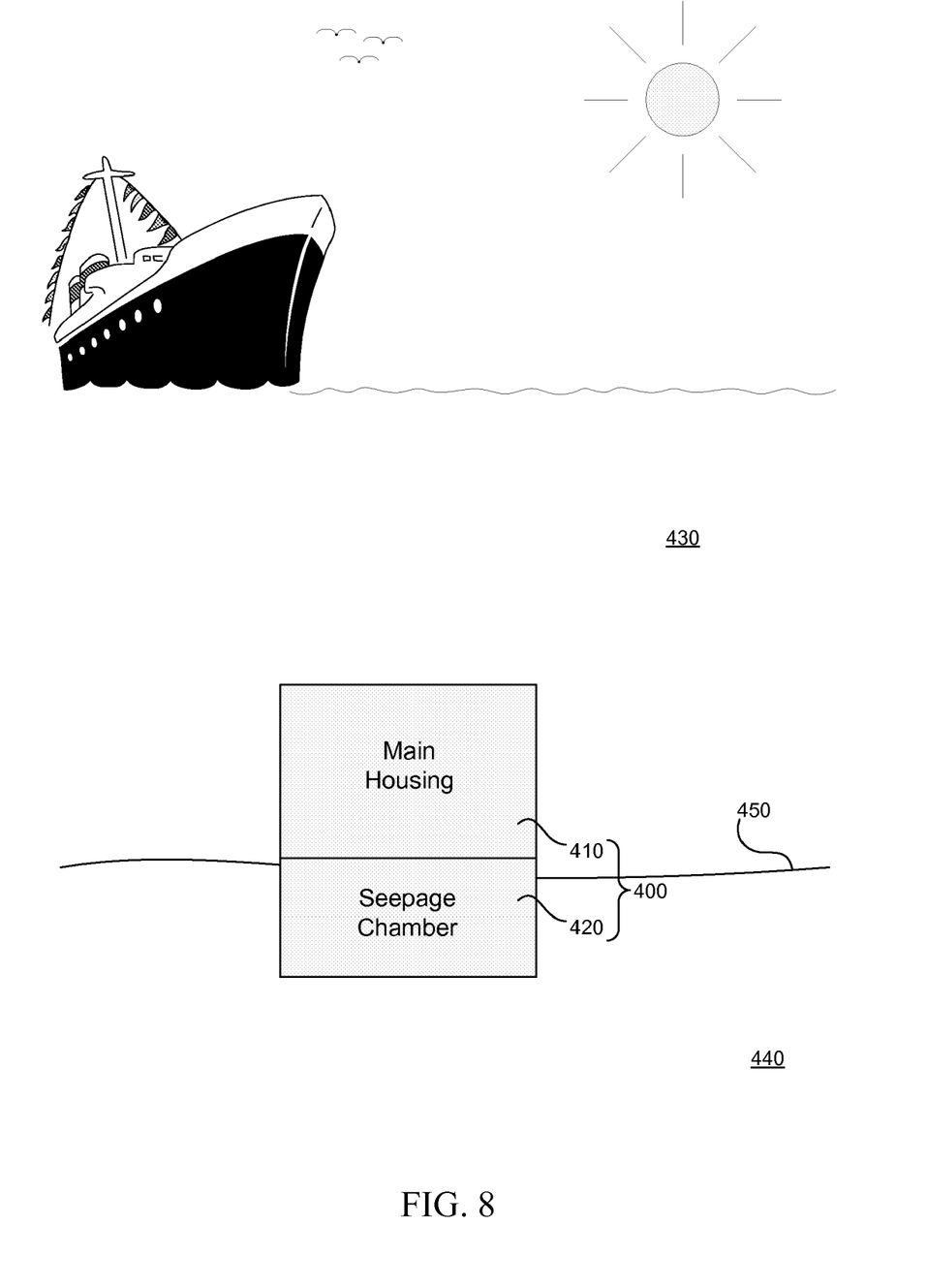
FIG. 8 shows a block diagram of an embodiment of a tidal seepage meter that may be used to perform an embodiment of the method for sampling seepage, as implemented within a body of water.

FIG. 8 shows a block diagram of an embodiment of a tidal seepage meter (TSM) 400 that may be used in an embodiment of the method for sampling seepage, as implemented within the a body of water 430. TSM 400 may include main housing 410 and seepage chamber 420. TSM 400 may be positioned beneath body of water 430 and partially embedded in sediment 440. In one implementation, TSM 400 is positioned with seepage chamber 420 substantially embedded within sediment 440 so that sediment surface 450 may be substantially flush with the top of seepage chamber 420. In one implementation, one side of TSM 400 may be slightly higher than other sides of TSM 400 with respect to sediment surface 440 so that seepage flows through an outlet (not shown) of seepage chamber 420.

FIG. 9 shows a block diagram of an embodiment of a tidal seepage meter (TSM) 500 that may be used with a method for sampling seepage, such as methods 10, 100, and/or 200 as discussed herein. TSM 500 may include seepage chamber 560, which is analogous to seepage chambers 360 and 420 of FIGS. 6 and 8, respectively, and main housing 580, which is analogous to main housing 410 of FIG. 3. TSM 500 may be substantially similar to TSM 300 of FIG. 6, and thus, identical components are not described again in detail. Seepage chamber 560 further includes outlet conduit 562. Main housing 580 includes power and controller housing 582, stepper motor 540, selector valve 550 and first sampling container 570 and second sampling container 571. Power and controller housing may include power 410, relay 520 and controller 530. Selector valve 550 may further comprise outlet ports 572.

Seepage chamber 560 may be operatively coupled to selector valve 550 via outlet conduit 562. Seepage chamber 560 may be comprised of high density polyethylene. Seepage (represented by vertical and horizontal arrows in FIG. 9) may enter seepage chamber 560 from open end 564 and travel to selector valve 550 via outlet conduit 562. Controller 530 may be capable of receiving a sampling schedule. Controller 530 may be operatively coupled to motor relay 520 and inputs control signals to motor relay 520 according to the sampling schedule. Relay 520 may operatively couple power 510 and stepper motor 540 when activated by control signals from controller 530. Stepper motor 540 may actuate selector valve 550 when coupled to power 510 via relay 520. Selector valve 550 may be operatively coupled to seepage chamber 560 (via outlet conduit 562), stepper motor 540 and sample containers 570 and 571 (via outlet ports 572). Selector valve 550 may receive seepage from seepage chamber 560 via outlet conduit 562. Selector valve 550 may direct seepage to one of the sample containers 570 or 571 via outlet ports 572. Motor 540 may actuate selector valve 550 according to a sampling schedule, which selects one of the plurality of sample containers 570 and 571. Although FIG. 9 shows only two sample containers, those skilled in the art shall recognize that TSM 500 may comprise more than two sample containers (e.g., six sample containers) without departing from the scope or spirit of the present invention.

FIG. 10 shows a block diagram of an embodiment of a selector valve and sample container configuration for a tidal seepage meter that may be used in a method for sampling seepage, such as methods 10, 100, and/or 200 as discussed herein. The selector valve and sample container embodiment ("six-sample embodiment") 600 may include two four-way selector valves and six sample containers. As shown in FIG. 10, six-sample embodiment 600 may include selector valves 650 and 652 and sample containers 670. Inlet ports 656 of selector valves 650 and 652 may receive seepage from a seepage chamber via outlet conduits 662, which are analogous to outlet conduit 562 of FIG. 9. Selector valves 650 and 652 may input seepage to sample containers 670 via outlet ports 672. Stoppers 658 may cover selected outlet ports of selector valves 650 and 652.

Six-sample embodiment 600 may operate in the following manner. Initially, covered outlet ports of selector valves 650 and 652 may be selected. Thus, seepage cannot flow out of selector valves 650 and 652. When a first sampling time occurs according to a sampling schedule, a motor may actuate selector valve 650, which may rotate selector valve 650 90 degrees clockwise. Thus, seepage may flow from outlet conduit 662 to sample container 670 located at the 6 o'clock position of selector valve 650 via inlet port 656. At a second sampling time, the motor may actuate selector valve 650, which may rotate selector valve 650 90 degrees clockwise. Thus, seepage may flow from outlet conduit 662 to sample container 670 located at the 9 o'clock position of selector valve 650 via inlet port 656. At a third sampling time, the motor may actuate selector valve 650, which may rotate selector valve 650 90 degrees clockwise. Thus, seepage may flow from outlet conduit 662 to sample container 670 located at the 12 o'clock position of selector valve 650 via inlet port 656.

At a fourth sampling time, the motor may actuate selector valve 650, which may rotate selector valve 650 90 degrees clockwise, and may actuate selector valve 652, which may rotate selector valve 652 90 degrees clockwise. Thus, seepage may be prevented from flowing out of selector valve 650 due to stopper 658; and seepage may flow from outlet conduit 662 to sample container 670 located at the 12 o'clock position of selector valve 652 via inlet port 656. At a fifth sampling time, the motor may actuate selector valve 652, which may rotate selector valve 652 90 degrees clockwise. Thus, seepage may flow from outlet conduit 662 to sample container 670 located at the 3 o'clock position of selector valve 652 via inlet port 656. At a sixth sampling time, the motor may actuate selector valve 652, which may rotate selector valve 652 90 degrees clockwise. Thus, seepage may flow from outlet conduit 662 to sample container 670 located at the 6 o'clock position of selector valve 652 via inlet port 656. After the sixth sampling time, the motor may actuate selector valve 652, which may rotate selector valve 652 90 degrees clockwise. Thus, seepage may be substantially prevented from flowing in outlet conduit 662 due to stopper 658 located at the 9 o'clock position of selector valve 652.

Many modifications and variations of the Method for Sampling Seepage are possible in light of the above description. Therefore, within the scope of the appended claims, the Method for Sampling Seepage may be practiced otherwise than as specifically described. Further, the scope of the claims is not limited to the implementations and embodiments disclosed herein, but extend to other implementations and embodiments as may be contemplated by those having ordinary skill in the art.

We claim:

1. A method comprising the steps of:
   providing a tidal seepage meter comprising:
   a power supply,
   a controller, operatively coupled to the power supply, capable of controlling the power supply according to a sampling schedule,
   a motor, operatively coupled to the power supply, capable of receiving power from the power supply according to the sampling schedule,
   a selector valve comprising an input port and at least two outlet ports, operatively coupled to the motor, capable of selecting an output valve according to the sampling schedule, a seepage chamber, operatively coupled to the selector valve, capable of receiving seepage and inputting seepage to the selector valve via the input port, and a first sample container and a second sample container, operatively coupled to the selector valve via at least two output valves, capable of receiving seepage from the selector valve via the output valve;

transferring the sampling schedule to the tidal seepage meter, the sampling schedule having at least two sampling times;

positioning the tidal seepage meter in sediment; and sampling seepage according to the sampling schedule.

2. The method of claim 1, wherein the step of transferring the sampling schedule to the tidal seepage meter comprises the step of downloading the sampling schedule from a computer operatively coupled to the tidal seepage meter.

3. The method of claim 2, wherein the computer is contained within the tidal seepage meter.

4. The method of claim 1, wherein the step of positioning the tidal seepage meter in sediment comprises the steps of:

positioning the tidal seepage meter in sediment;

equilibrating the tidal seepage meter; and activating the tidal seepage meter.

5. The method of claim 1, wherein the step of sampling seepage according to the sampling schedule comprises the steps of:

determining whether scheduled rotation time has occurred;

if the rotation time has not occurred, then returning to the step of determining whether scheduled rotation time has occurred;

if the rotation time has occurred, then rotating a selector valve;

determining whether sampling is complete;

if sampling is not complete, returning to the step of determining whether scheduled rotation time has occurred; and if sampling is complete, rotating the selector valve to a plugged port.

6. The method of claim 1, wherein the step of sampling seepage according to the sampling schedule comprises the step of:

sampling seepage during a first sampling time in the first sample container; and sampling seepage during a second sampling time in the second sample container.

7. The method of claim 1 further comprising the step of preparing the tidal seepage meter before the step of positioning the tidal seepage meter in sediment.

8. The method of claim 7, wherein the step of preparing the tidal seepage meter comprises the step of cleaning all plumbing of the tidal seepage meter.

9. The method of claim 1 further comprising the steps of:

retrieving the first sample container and the second sample container; and analyzing the seepage from the first sample container and the second sample container to determine properties of the seepage.

10. The method of claim 9 further comprising the step of displaying the properties of the seepage to a user via a display device.

11. The method of claim 10, wherein the display device is a computer display.

12. A method for sampling seepage comprising the steps of:

providing a tidal seepage meter comprising:

a power supply, a controller, operatively coupled to the power supply, capable of controlling the power supply according to a sampling schedule, a motor, operatively coupled to the power supply, capable of receiving power from the power supply according to the sampling schedule, a selector valve comprising an input port and at least two outlet ports, operatively coupled to the motor, capable of selecting an output valve according to the sampling schedule, a seepage chamber, operatively coupled to the selector valve, capable of receiving seepage and inputting seepage to the selector valve via the input port, and a first sample container and a second sample container, operatively coupled to the selector valve via at least two output valves, capable of receiving seepage from the selector valve via the output valve;

transferring the sampling schedule to the tidal seepage meter, the sampling schedule having at least two sampling times;

cleaning all plumbing of the tidal seepage meter;

positioning the tidal seepage meter in sediment;

sampling seepage during a first sampling time in the first sample container; and sampling seepage during a second sampling time in the second sample container.

13. The method for sampling seepage of claim 12, wherein the step of transferring the sampling schedule to the tidal seepage meter comprises the step of downloading the sampling schedule from a computer operatively coupled to the tidal seepage meter.

14. The method for sampling seepage of claim 13, wherein the computer is contained within the tidal seepage meter.

15. The method for sampling seepage of claim 12, wherein the step of positioning the tidal seepage meter in sediment comprises the steps of:

positioning the tidal seepage meter in sediment;

equilibrating the tidal seepage meter; and activating the tidal seepage meter.

16. A method for sampling seepage comprising the steps of:

providing a tidal seepage meter comprising:

a power supply, a controller, operatively coupled to the power supply, capable of controlling the power supply according to a sampling schedule, a motor, operatively coupled to the power supply, capable of receiving power from the power supply according to the sampling schedule, a selector valve comprising an input port and at least two outlet ports, operatively coupled to the motor, capable of selecting an output valve according to the sampling schedule, a seepage chamber, operatively coupled to the selector valve, capable of receiving seepage and inputting seepage to the selector valve via the input port, and a first sample container and a second sample container, operatively coupled to the selector valve via at least two output valves, capable of receiving seepage from the selector valve via the output valve;

transferring the sampling schedule to the tidal seepage meter, the sampling schedule having at least two sampling times;

positioning the tidal seepage meter in sediment;

sampling seepage according to the sampling schedule;

retrieving the first sample container and the second sample container;

analyzing the seepage from the first sample container and the second sample container to determine properties of the seepage; and displaying the properties of the seepage to a user via a display device.

17. The method for sampling seepage of claim 16, wherein the step of sampling seepage according to the sampling schedule comprises the steps of:

determining whether scheduled rotation time has occurred;

if the rotation time has not occurred, then returning to the step of determining whether scheduled rotation time has occurred;

if the rotation time has occurred, then rotating a selector valve;

determining whether sampling is complete;

if sampling is not complete, returning to the step of determining whether scheduled rotation time has occurred; and if sampling is complete, rotating the selector valve to a plugged port.

18. The method for sampling seepage of claim 16, wherein the step of sampling seepage according to the sampling schedule comprises the step of:

sampling seepage during a first sampling time in the first sample container; and sampling seepage during a second sampling time in the second sample container.

19. The method for sampling seepage of claim 16, wherein the display device is a computer display.

* * * * *